United States Patent [19]

McRae

[11] Plant 4,933

[45] Nov. 9, 1982

[54] LILY PLANT: LILIUM 'UTOPIA'

[75] Inventor: Edward A. McRae, Boring, Oreg.

[73] Assignee: Melridge, Inc., Sandy, Oreg.

[21] Appl. No.: 258,743

[22] Filed: Apr. 29, 1981

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant bearing large clusters of large flowers of excellent form, unusual color, and long persistence, both on the plant and as cut flowers. The plant is characterized by rapid and natural propagation under field conditions and vigorous and healthy growth when forced under glass. It is further characterized by its regular and attractive inflorescence, the brilliant yellow color of its buds, the large size of its flowers, the great width and thickness of its tepals, the inconspicuous character of its tepal spotting, and the brilliant lemon yellow color of its flowers.

2 Drawing Figures

BACKGROUND AND GENERAL STATEMENT OF THE INVENTION

My new variety of lily plant is classified botanically as a Lilium hybrid, commercially as an upright Asiatic hybrid Division I-A in the Horticultural Classification of the Genus Lilium adopted by the Royal Horticultural Society of London.

My new variety of lily plant originated as a seedling selected from a group of seedlings among the seedling beds of test crosses at Oregon Bulb Farms, Sandy, Oreg. The breeding program was initiated in 1965 and the lily plant first flowered in 1970.

The cross was made during a breeding program having as its objective the production of brilliant yellow, unspotted or lightly spotted, upright-flower cultivars which would perform adequately when forced into flower under glass throughout the year, in addition to meeting the requirements of vigor, disease resistance, and rapid natural propagation in field growth. Cultivars were sought which would be disease resistant, virus tolerant, and not overly susceptible to leaf scorch or bud abortion when forced under glass.

The cross was made between the seed parent {'Uncle Sam' × [('Mega' × 'Lemon Queen') × 'Edith Cecilia']} (not patented) and the pollen parent 'Connecticut King' (unpatented).

My new lily plant is characterized by rapid and natural propagation under field conditions and by vigorous and healthy growth when forced under glass without excessive leaf scorch and bud abortion. It shows uniform qualities of growth to maturity when forced into flowers throughout the year. Its bud and flowers are exceptionally large, and brilliant lemon yellow in color.

Lilium 'Utopia' most closely resembles the older cultivars Lilium 'Dayspring' (U.S. Plant Pat. No. 4,181) and Lilium 'Connecticut King', the latter being its pollen parent. However, it is much superior to 'Connecticut King' in its larger flower size, greater tepal width and thickness, regularly shaped and more attractive inflorescence, and longer lasting flowers. It differs from 'Dayspring' in that its tepal thickness is greater, its color somewhat more intense and deeper, and its flower virtually spotless (the spotting is tiny and inconspicuous).

My new variety of lily plant has been asexually reproduced by me and under my direction at Oregon Bulb Farms in Sandy, Oreg. Successive generations produced by bulb scale propagation and natural propagation from bulblets have demonstrated that the novel and distinctive characteristics of my new variety are fixed and hold true under asexual propagation from generation to generation.

THE DRAWING

My new variety of lily plant is illustrated in the accompanying photographic drawing which shows the plant, its foliage, and its buds in their various stages of development and the open bloom in full color.

DESCRIPTION OF THE NEW VARIETY

The following is a detailed description of my new variety of the Asiatic hybrid lily with nomenclature according to the International Lily Register (Royal Horticultural Society of London, Second Edition 1969) and with color designations according to the Royal Horticultural Society Color Chart, published by the Royal Horticultural Society in 1966.

THE PLANT

Form: Bulbous monocotyledon.

Height: Bulbs 12–15 cm in circumference produce stems 80–95 cm (32–38") tall when forced into flower under glass; field-grown bulbs produce stems 80–110 cm (32–44") tall in their second season after scaling.

Growth: Extremely vigorous and strong.

Foliage: Abundant, with about 80–100 leaves per stem.

*Size of leaves.*—6–10 cm ($2\frac{1}{4}$–4") long and 1.5–2.0 cm ($\frac{5}{8}$–$\frac{3}{4}$") wide.

*Shape of leaves.*—Lanceolate.

*Texture of leaves.*—Leaves entire (not serrated), smooth and glossy on upper sides and lower sides, but margins lightly pubescent.

*Color of leaves, upper side.*—Deep green.

*Color of leaves, under side.*—Medium to deep green.

*Ribs and veins of leaves.*—Typical monocotyledonous venation; light green parallel veins.

INFLORESCENCE

Well-spaced pyramidal raceme with ascending pedicels and no secondary buds. Bulbs which are 12–15 cm (5–6") in circumference produce 7–9 buds.

Peduncle and pedicel: Hairy. Very lightly pubescent. Buds are also lightly pubescent.

Strength of inflorescence: Strong and wirey; does not require staking.

Color of inflorescence: Deep green with soft purple overlay. Buds are brilliant lemon yellow when mature.

THE BUDS

Size: 7–9 cm (3–3¼″) long; 2–5 cm (¾–1¼″) wide.

Form: Lanceolate with obtuse tip; typical of Asiatic hybrid lilies.

Opens slowly: Opens in about one hour in response to morning light; flowers further up the stem open on subsequent days over an interval of 1–2 weeks. Typical of Asiatic hybrid lilies.

Color of mature buds: Brilliant lemon yellow (RHS CC #6A) with purple-brown pigment on the extreme outer tepal tips.

THE FLOWER

Blooming characteristics: Flowers in midseason, late June and early July in western Oregon, once, and profusely.

Flower size: Flower diameter is 14–17 cm (5½–7″). Inner tepals are 4.0–4.5 cm (1½–1¾″) wide. Outer tepals are 2.5–3.0 cm (¾–1″) wide.

Shape when flower first opens: Shallow bowl-shape with lightly recurved tepal tips. Tepals recurve more as flower ages.

Tepal arrangement: Typical of the genus Lilium, with 6 entire, imbricated tepals.

*Color, outer tepal.*—Brilliant lemon yellow (Royal Horticultural Society's Color Code #6A), shading to deeper yellow (RHS CC #9A) as the flower ages.

*Color, base of tepal.*—Brilliant lemon yellow (RHS CC #6A) shading to deeper yellow (RHS CC #9A) as flower ages.

*Color, inside tepals.*—Brilliant lemon yellow (RHS CC #6A) shading to deeper yellow (RHS CC #9A) as flower ages.

*Color, reverse of tepal.*—Brilliant lemon yellow (RHS CC #8A).

*Spotting pattern.*—A few very tiny and inconspicuous purple-pigmented papillae, parallel to nectaries, at center of tepals only.

*Tepal duration.*—Tepals remain on individual flower for 5–7 days; stem has flowers with tepals adhering for about 3 weeks. Tepals fall as flower ages.

Flower texture: Shiny, velvety. Not affected by hot or wet weather.

Pedicel: Pedicel is sturdy and upright, ascending at 45-degree angle.

*Length.*—5–12 cm (2–5″).

*Color.*—Dark green with soft purple overlay.

Disease resistance: Resistant to Botrytis blight and to Fusarium bulb rot.

Fragrance: None.

Lasting quality: Flowers remain on plants for about 3–4 weeks. Flowers remain on cut-flower stems for about 3 weeks, with adequate light.

THE REPRODUCTIVE ORGANS

Stamens and anthers: Typical of genus Lilium. Six versatile anthers hang (singly) from 6 narrow filaments.

Filaments: 5–6 cm (2″) long and light yellow.

Pollen: Gold to slightly brownish gold.

Pistil: 1, typical of genus Lilium. Style is 5–6 cm (2″) long.

Stigma: Small, soft plum in color, and 3-lobed.

Ovary: Typical of genus Lilium. Superior, single, 6-chambered ovary.

THE FRUIT

Fertile, an ovoid to oblong capsule with 6 chambers.

Color at maturity: Medium green to dark green, sometimes overlaid with soft purple. Fades to soft brown when fruit splits open to release seeds.

THE BULBS

Color of bulbs: White.

Size of bulbs: Usual commercial size is 12–20 cm (5–8″) in circumference; bulbs can be grown to a much larger size if this is desired.

I claim:

1. A new and distinctive variety of Asiatic hybrid lily plant, substantially as herein shown and described, characterized by its rapid natural propagation under field conditions; its vigorous and healthy growth when forced under glass; its regular and attractive inflorescence; the brilliant lemon yellow color of its buds; the large size of its flowers; the great width and thickness of its tepals; the inconspicuous character of its tepal spotting; the brilliant lemon yellow color of its flowers; and the long life of its flowers.

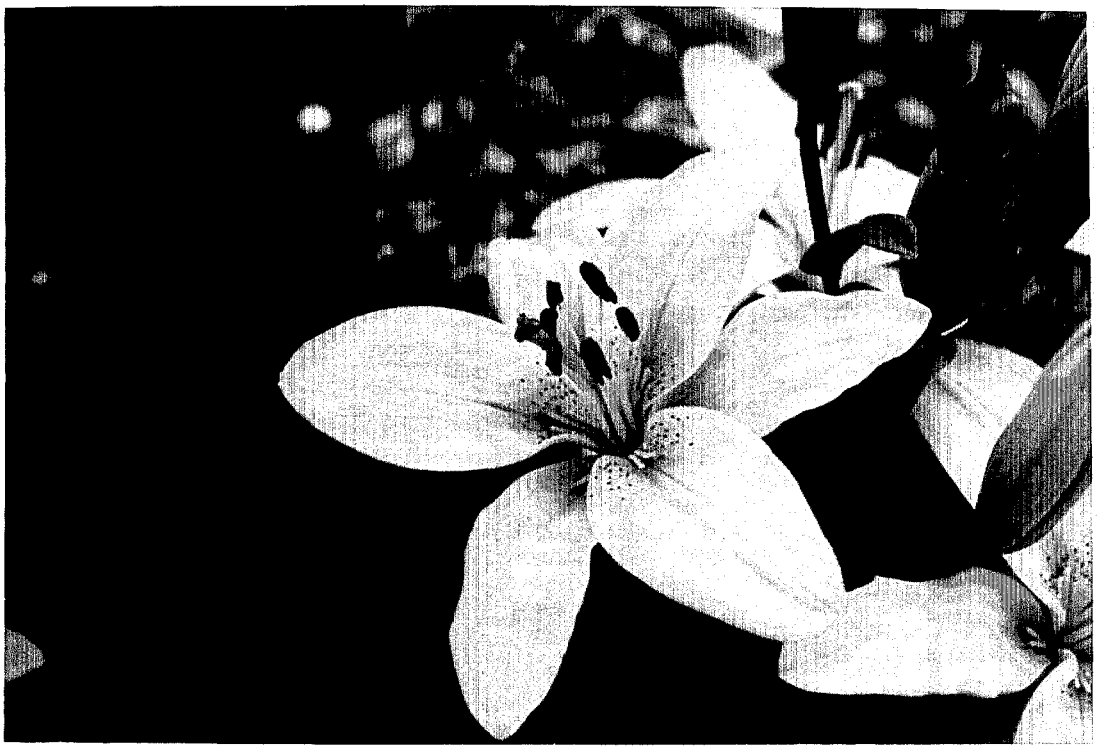
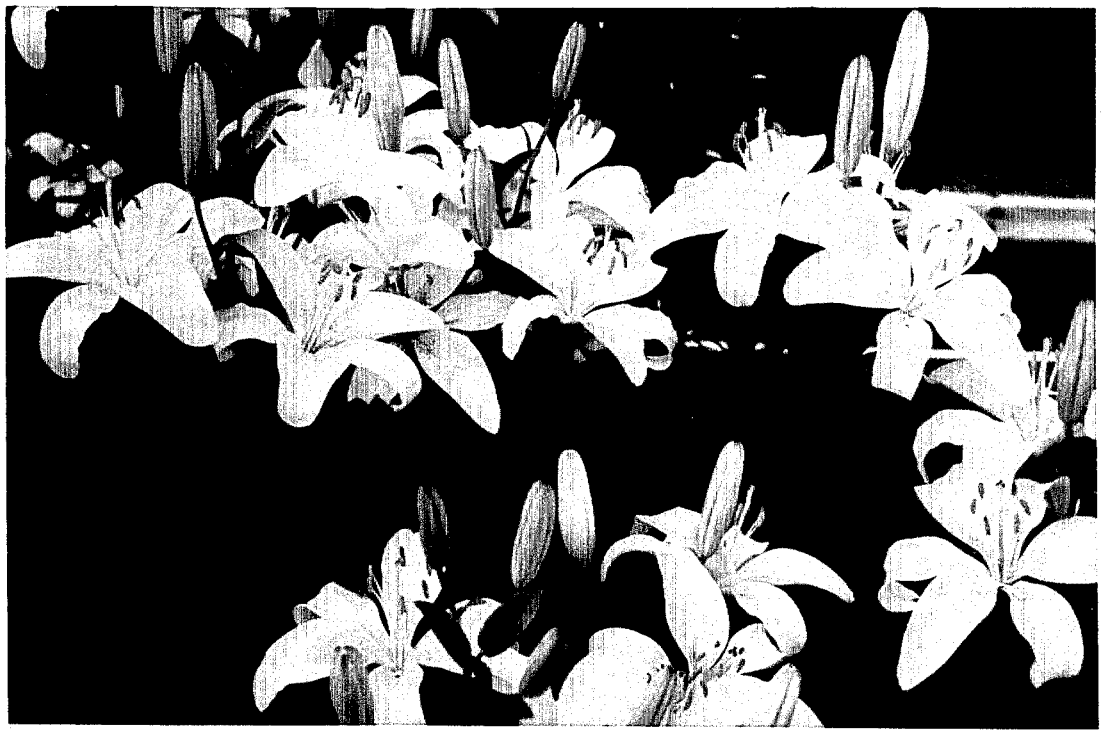

* * * * *